United States Patent [19]
Selmon et al.

[11] Patent Number: 6,010,449
[45] Date of Patent: Jan. 4, 2000

[54] INTRAVASCULAR CATHETER SYSTEM FOR TREATING A VASCULAR OCCLUSION

[75] Inventors: Matthew R. Selmon, Woodside; Gerald Hansen, Newark; Charles Milo, Union City, all of Calif.

[73] Assignee: LuMend, Inc., Redwood City, Calif.

[21] Appl. No.: 08/808,527

[22] Filed: Feb. 28, 1997

[51] Int. Cl.⁷ .......................... A61B 1/005; A61M 29/00
[52] U.S. Cl. .................. 600/117; 600/137; 600/146; 600/104; 604/96; 606/198
[58] Field of Search ................. 600/114, 115, 600/116, 117, 137, 146; 606/194, 198; 604/96

[56] References Cited

U.S. PATENT DOCUMENTS

| | | |
|---|---|---|
| Re. 32,158 | 5/1986 | Vukovic ................. 600/154 |
| 832,201 | 10/1906 | Kistler . |
| 1,127,948 | 2/1915 | Wappler ................. 600/104 |
| 1,267,066 | 5/1918 | Flack . |
| 2,621,651 | 12/1952 | Wallace ................. 600/104 |
| 3,640,270 | 2/1972 | Hoffman . |
| 3,667,474 | 6/1972 | Lapkin et al. . |
| 4,043,323 | 8/1977 | Komiya . |
| 4,355,643 | 10/1982 | Laughlin et al. . |
| 4,541,433 | 9/1985 | Baudino . |
| 4,572,186 | 2/1986 | Gould et al. . |
| 4,585,000 | 4/1986 | Hershenson . |
| 4,630,609 | 12/1986 | Chin . |
| 4,648,402 | 3/1987 | Santos . |
| 4,669,467 | 6/1987 | Willett et al. . |
| 4,681,110 | 7/1987 | Wiktor . |
| 4,698,057 | 10/1987 | Joishy . |
| 4,723,549 | 2/1988 | Wholey et al. . |
| 4,737,142 | 4/1988 | Heckele ................. 600/116 |
| 4,787,388 | 11/1988 | Hofmann . |
| 4,794,928 | 1/1989 | Kletschka . |
| 4,848,336 | 7/1989 | Fox et al. . |
| 4,862,874 | 9/1989 | Kellner ................. 600/116 |
| 4,919,112 | 4/1990 | Siegmund . |
| 5,001,556 | 3/1991 | Nakamura et al. . |

(List continued on next page.)

| | | |
|---|---|---|
| 5,649,941 | 7/1997 | Lary . |
| 5,653,684 | 8/1997 | Laptewicz et al. . |
| 5,662,671 | 9/1997 | Barbut et al. . |
| 5,688,234 | 11/1997 | Frisbie . |
| 5,707,390 | 1/1998 | Bonutti . |
| 5,713,907 | 2/1998 | Hogendijk et al. . |
| 5,800,450 | 9/1998 | Lary ........................... 606/194 |
| 5,816,923 | 10/1998 | Milo et al. . |
| B1 4,919,112 | 12/1993 | Siegmund . |

FOREIGN PATENT DOCUMENTS

| | | |
|---|---|---|
| 0 377 269 A1 | 7/1990 | European Pat. Off. . |
| 0 521 595 A2 | 7/1993 | European Pat. Off. . |
| 1585065 | 9/1970 | France . |
| 2945237 A1 | 5/1981 | Germany . |
| 4429117 A1 | 2/1996 | Germany . |
| 134398 | 1/1960 | U.S.S.R. . |
| WO83/03188 | 9/1983 | WIPO . |
| WO91/19528 | 12/1991 | WIPO . |
| WO92/08510 | 5/1992 | WIPO . |
| WO93/18818 | 9/1993 | WIPO . |
| WO95/19143 | 7/1995 | WIPO . |
| WO96/01590 | 1/1996 | WIPO . |
| WO96/11636 | 4/1996 | WIPO . |

*Primary Examiner*—John P. Leubecker
*Attorney, Agent, or Firm*—Wilson, Sonsini, Goodrich & Rosati

[57] ABSTRACT

An intravascular catheter system for crossing a severe or total arterial occlusion includes a steerable intravascular catheter providing a working element and an optical guidance system. The optical guidance system is realized by an optical member with may include an imaging shaft that is rotated and measured by a motor/encoder assembly or which may include an optical switching device connected to a plurality of optical fibers. The working element may include a plurality of opening members that are actuated by an external plunger.

24 Claims, 11 Drawing Sheets

U.S. PATENT DOCUMENTS

| | | |
|---|---|---|
| 5,011,488 | 4/1991 | Ginsburg . |
| 5,019,040 | 5/1991 | Itaoka et al. . |
| 5,030,201 | 7/1991 | Palestrant . |
| 5,034,001 | 7/1991 | Garrison et al. . |
| 5,092,839 | 3/1992 | Kipperman . |
| 5,098,381 | 3/1992 | Schneider . |
| 5,099,850 | 3/1992 | Matsui et al. . |
| 5,100,425 | 3/1992 | Fischell et al. . |
| 5,102,390 | 4/1992 | Crittenden et al. ........................ 604/96 |
| 5,114,414 | 5/1992 | Buchbinder . |
| 5,179,961 | 1/1993 | Littleford et al. . |
| 5,180,368 | 1/1993 | Garrison . |
| 5,192,290 | 3/1993 | Hilal . |
| 5,193,546 | 3/1993 | Shaknovich . |
| 5,209,729 | 5/1993 | Hofmann et al. . |
| 5,211,654 | 5/1993 | Kaltenbach . |
| 5,217,484 | 6/1993 | Marks . |
| 5,263,959 | 11/1993 | Fischell . |
| 5,263,963 | 11/1993 | Garrison et al. . |
| 5,279,565 | 1/1994 | Klein et al. . |
| 5,282,817 | 2/1994 | Hoogeboom et al. . |
| 5,304,199 | 4/1994 | Myers . |
| 5,321,501 | 6/1994 | Swanson et al. . |
| 5,334,210 | 8/1994 | Gianturco . |
| 5,336,252 | 8/1994 | Cohen . |
| 5,350,377 | 9/1994 | Winston et al. . |
| 5,351,678 | 10/1994 | Clayton ................................... 600/141 |
| 5,383,467 | 1/1995 | Auer et al. . |
| 5,409,453 | 4/1995 | Lundquist et al. . |
| 5,415,636 | 5/1995 | Forman . |
| 5,423,846 | 6/1995 | Fischell ................................... 606/108 |
| 5,439,000 | 8/1995 | Gunderson et al. . |
| 5,456,667 | 10/1995 | Ham et al. . |
| 5,459,570 | 10/1995 | Swanson et al. . |
| 5,484,412 | 1/1996 | Pierpont ................................... 604/101 |
| 5,486,170 | 1/1996 | Winston et al. . |
| 5,486,193 | 1/1996 | Bourne et al. . |
| 5,490,859 | 2/1996 | Mische et al. . |
| 5,499,995 | 3/1996 | Teirstein . |
| 5,501,694 | 3/1996 | Ressemann et al. . |
| 5,507,295 | 4/1996 | Skidmore . |
| 5,507,296 | 4/1996 | Bales et al. . |
| 5,511,559 | 4/1996 | Vance . |
| 5,522,819 | 6/1996 | Graves et al. . |
| 5,540,707 | 7/1996 | Ressemann et al. . |
| 5,573,531 | 11/1996 | Gregory . |
| 5,599,306 | 2/1997 | Klein et al. . |
| 5,618,300 | 4/1997 | Marin et al. . |
| 5,626,599 | 5/1997 | Bourne et al. . |
| 5,626,607 | 5/1997 | Malecki et al. . |

INTRAVASCULAR CATHETER SYSTEM FOR TREATING A VASCULAR OCCLUSION

This application is related to U.S. patent applications Ser. No. 08/775,264 filed on Feb. 28, 1997, and Ser. No. 09/032,770 filed on Feb. 28, 1998 which claims priority to U.S. Provisional Patent Application 60/038,531 filed on Feb. 28, 1997.

BACKGROUND OF THE INVENTION

1. Field of the Invention

This invention relates generally to medical devices and especially intravascular catheters designed to operate on occlusions within an artery. More particularly, this invention relates to intravascular catheters able to operate on an obstruction within an artery even if that obstruction forms a total occlusion of the artery passageway.

2. Background

Medical science has long sought effective treatments for disease conditions involving stenosis (narrowing or obstruction) of the lumen (interior passage) of an artery. This condition, known generally as an occlusion, is found in patients suffering from atherosclerosis (accumulation of fibrous, fatty or calcified tissue in the arteries). An occlusion can manifest itself in hypertension (high blood pressure), ischemia (deficiency of circulation), angina (chest pain), myocardial infarction (heart attack), stroke, or death. An occlusion may be partial or total, may be soft and pliable or hard and calcified, and may be found at a great variety of sites in the arterial system including the aorta, the coronary and carotid arteries, and peripheral arteries.

Of particular interest to cardiac medicine are the often disabling or fatal occlusions occurring in the coronary arteries (arteries supplying the heart). Traditionally, coronary artery occlusions have been treated by performing coronary bypass surgery, in which a segment of the patient's saphenous vein is taken from the patient's leg and is grafted onto the affected artery at points proximal (upstream) and distal (downstream) to the occluded segment. The bypass often provides dramatic relief. However, it entails dangerous open chest surgery and a long, painful, costly convalescence in the hospital. Moreover, with the passage of time, the bypass patient's saphenous vein graft can also become occluded. If the patient has another saphenous vein, a second bypass procedure may be performed, once again entailing open chest surgery and prolonged hospitalization. Thereafter, if the underlying atherosclerotic disease process is not controlled, the prognosis is dismal.

Newer, minimally invasive procedures are now preferred in the treatment of arterial occlusions. These procedures use a catheter, a long, thin, highly flexible device which is introduced into a major artery through a small arterial puncture made in the groin, upper arm, or neck and is advanced and steered into the site of the stenosis. At the distal end of the catheter, a great variety of miniature devices have been developed for operating upon the stenosed artery.

The more popular minimally invasive procedures include percutaneous transluminal coronary angioplasty (PTCA), directional coronary atherectomy (DCA), and stenting. PTCA employs a balloon to mechanically dilate the stenosis. In PTCA, a steerable guidewire is introduced and advanced under fluoroscopic observation into the stenosed artery and past the stenosis. Next, a balloon-tipped catheter is advanced over the guidewire until it is positioned across the stenosed segment. The balloon is then inflated, separating or fracturing the atheroma (stenosed tissue). The hoped-for outcome is that, over time, the lumen will stay open.

In directional coronary atherectomy, a catheter containing a cutter housed in its distal end is advanced over the guidewire into the stenosed segment. The housing is urged against the atheroma by the inflation of a balloon, so that part of the atheroma intrudes through a window in the side of the housing. Under fluoroscopic observation, the cutter is used to shave away the atheroma. The shavings are collected in the nosecone of the housing and withdrawn along with the catheter.

Stenting is a procedure in which a wire framework, known as a stent, is compressed and delivered a balloon catheter. The stent is positioned across the stenosed segment of the artery. The balloon is inflated, dilating the stent and forcing the stent against the artery wall. The hoped-for outcome is that the stent will hold the arterial lumen open for a prolonged period. Frequently, a stent is placed in an artery immediately following PTCA or DCA.

It must be noted, however, that the aforementioned catheters are "over-the-wire catheters." These catheters depend on the guidewire, which typically has a tiny bent portion at its distal end for steering. Over-the-wire catheters cannot be positioned adjacent the stenosis until the guidewire has been advanced across the stenosed arterial segment. Thus, where the occlusion is too severe to be crossed by a guidewire or where there is not enough room for the balloon, cutter, or stent delivery catheter, neither PTCA nor DCA nor stenting can be done. Unfortunately, the occlusion often contains extremely hard, calcified tissue and presents an impenetrable barrier to the guidewire. Even a less than total occlusion may contain complex structures which divert or trap the steering end of the guidewire. Thus, the guidewire might not completely cross the occlusion, but become diverted into the subintimal space between the intima and the atheroma or become buried in the atheroma. In either case, the guidewire cannot be positioned across the stenosis to guide a balloon or cutting element. In such cases, bypass surgery may be necessary with the associated cost, risks, and recovery period.

Thus, in patients suffering from severe or total arterial occlusion, it is preferable to do what has been difficult or impossible in the past: to open the severely or totally occluded artery itself, rather than by performing a bypass. If a guidewire and working catheter can be passed through or around the atheroma, the severe or total occlusion can be treated by PTCA, DCA, stenting, site-specific drug delivery or a combination of these proven therapies.

It would be advantageous to find and open a path of low resistance, either through or around the atheroma. Of course, this must be done without perforating the arterial wall. Clearly, the serious consequences of penetrating the arterial wall must be avoided at all costs. The physician will not use a system which would be unsafe and no patient would want a physician to use such a system. Therefore, any solution to the problem of finding and creating an opening through or around the atheroma must be safe and, in many instances, must include a system of guidance for the device that would find and open such an occlusion.

There has been a long felt need to provide a reliable guidance system for such a device. As understood by those in the art, the device must traverse a criss-crossing, often maze-like structure before it even reaches the occlusion. Then the occlusion itself is often a maze like structure. Attempting to cross such an occlusion without reliable guidance is dangerous. For example, it is easy to dissect the tissues of the arterial wall instead of the occlusion, thereby creating a false lumen and possibly perforating the artery. If blood escapes the artery and accumulates in the pericardial space, it will compress the heart, requiring emergency intervention to avert heart failure and death.

One guidance system which has been used in conjunction with coronary catheterization is biplane fluoroscopy, wherein the interventionist observes two flat real-time x-ray images acquired from different angles. Biplane fluoroscopy, however, is unreliable, costly, and slow. Delay is unacceptable, for it contributes to trauma and stress and creates opportunities for complications and failures of technique.

Recently, promising optical systems have been disclosed for imaging an occlusion through a catheter placed in the artery. One such system is Optical Coherence Tomography (OCT). In OCT, a beam of light carried by an optical fiber illuminates the artery interior. In a radar-like manner, light reflected back into the fiber from features inside the artery is correlated with the emitted light to capture the depth as well as the angular separation of those features. The features are displayed graphically in two or three dimensions through the use of a suitably programmed computer.

The beam in OCT is swept by mechanical rotation or movement of optical components in the catheter, or by optical switching devices which select one of several fibers through which to perform measurements. The rotation is encoded, or the switching pattern recorded, to reconstruct angular information about the artery interior. For example, a beam splitter may be placed between the light source and the catheter fiber to produce a reference beam which is directed to a reflector at a known distance. The catheter beam and the reference beam are recombined as they return. When the paths traveled by the two beams are of equal optical length, interference fringes are observable in the combined beam. Since the lengths of the reference path and the catheter fiber are known, the distance from the fiber end to a particular reflective feature within the artery can be inferred. In OCT and related methods, signals may also be impressed upon the light beam to facilitate the measurement of distance or the detection of motion of objects relative to the fiber end. By means of OCT or other similar optical methods, imaging capability can be incorporated into an intravascular catheter or guidewire.

However, while superior imagery alone is of diagnostic interest, effective intervention for severe occlusive arterial disease is what is truly desired. What is needed is an intravascular catheter system for the effective treatment of the severely occluded artery and, in particular, the totally occluded artery, providing a combination of optical guidance and therapeutic intervention. What is especially needed is such an intravascular catheter system which allows the physician to effectively guide a working element of a catheter through a severe or total arterial occlusion with the benefit of an optical image obtained from within the artery.

SUMMARY OF THE INVENTION

It is an object of this invention to provide an intravascular catheter system for the effective treatment of the occluded artery. It is a corollary aspect of this invention to provide such an intravascular catheter system for treating the severely or totally occluded artery.

It is an additional object of this invention to provide an intravascular catheter system for guiding a working element in crossing a severe or total occlusion of an artery.

It is an additional object of this invention to provide an intravascular catheter system including optical imaging of an arterial occlusion during guidance of the working element into and across a chosen part of the occlusion.

In accordance with the above objects and those that will be mentioned and will become apparent below, an intravascular catheter system for the effective treatment of occlusions within an artery is provided which comprises:

an elongated flexible catheter shaft including a proximal end having a proximal end zone, a distal end having a distal end zone, and multiple lumina between the proximal and distal ends;

a steering apparatus disposed within the catheter shaft for steering the catheter shaft;

an imaging member located at the distal end of the catheter shaft for acquiring an image of the artery interior proximate the distal end; and a therapeutic element located at the distal end zone for treating the occlusion, whereby the therapeutic element is manipulable at the occlusion while the occlusion is imaged.

In addition, in accordance with the above objects and those that will be mentioned and will become apparent below, a method for the treatment of an occlusion within the artery is provided which comprises the steps of:

providing a multilumen catheter shaft having a distal end including an imaging apparatus, a steering apparatus, and a working element, the working element, steering apparatus and imaging apparatus being operative through the catheter shaft;

inserting the catheter shaft into the arterial system through a puncture in an artery;

advancing the distal end of the catheter shaft to the proximity of an occlusion within an artery;

manipulating the steering shaft and catheter shaft to direct the imaging member to the occlusion within the artery;

imaging the occlusion through the imaging member while manipulating the steering apparatus, catheter shaft to direct the working element to a desired portion of the occlusion;

operating the working element to create an opening through the occlusion within the artery true lumen; and inserting a guidewire through the occlusion.

The physician, having effectively opened a path across the occlusion using the apparatus and method of the instant invention, is now free to use a method of choice to treat the occlusion. For example, the physician may perform DCA or PTCA, install a stent, or use other techniques as appropriate.

The intravascular catheter system of the present invention provides a steering apparatus, imaging member and therapeutic element within a multilumen catheter shaft. In one embodiment of the intravascular catheter system, a rotatable imaging shaft is disposed within the catheter shaft. The imaging shaft contains an optical fiber which is connected to external optical instruments. At the distal end of the imaging shaft, the optical fiber conducts light from the instruments to illuminate the environment inside the artery and receives optical radiation returned from the environment. The imaging shaft is turned by an external motor-encoder which also measures the rotation of the shaft. As the imaging shaft rotates, the optical beam sweeps circumferentially about the longitudinal axis of the imaging shaft at a fixed angle from the longitudinal axis of the imaging shaft, illuminating different portions of the environment within the artery. The instruments correlate the emitted and received optical data with the rotational data to display an image of the interior of the artery.

In another exemplary, a steering apparatus is disposed within the catheter shaft and includes at least one wire attached at the distal end of the catheter shaft or of a steering shaft disposed in a lumen of the catheter shaft. When the wire is pulled, the distal end of the catheter shaft or steering shaft or both, as the case may be, is urged in the desired direction.

In another exemplary, an occlusion crossing wire is also disposed within the catheter shaft. The distal end of the crossing wire is advanced into the occlusion by pressure applied to the proximal end of the crossing wire, or by advancing the catheter shaft, or both.

In the operation of this embodiment of the intravascular catheter system, the physician introduces the catheter shaft over a previously introduced guidewire and positions the distal end of the catheter shaft proximate the occlusion. The physician observes the image generated by the instruments and selects a path for crossing the occlusion. The physician then steers the distal end of the intravascular catheter system by manipulating the steering apparatus, and operates the working element to cross the occlusion. It is an advantage of this embodiment of the intravascular catheter system that an image is acquired through as few as one optical fiber.

In another exemplary embodiment of the intravascular catheter system, an alternative imaging member is provided. In this embodiment, a plurality of optical fibers are disposed in an imaging shaft within the catheter shaft or disposed in the catheter shaft itself. At the distal end of the imaging shaft (or catheter shaft, as the case may be), the optical fibers conduct optical radiation from the instruments to illuminate the environment inside the artery and receive optical radiation returned from the environment. In conjunction with the external instruments, an optical switching device selectively connects the fibers to the external instruments and the optical data sampled from the different fibers are combined to generate and display an image of the artery interior. It is an advantage of this embodiment that there is no need for an external motor-encoder to drive the imaging shaft with respect to the catheter shaft.

In other exemplary embodiments in accordance with the invention, a balloon is disposed on the outer surface of the distal end zone of the catheter shaft. It is an advantage of these embodiments that, by inflating the balloon, the intravascular catheter system can be stabilized relative to the artery and occlusion while the steering apparatus and working element are manipulated and the imaging member provides images to the physician.

In the exemplary embodiments of the intravascular catheter system, at least one lumen communicating with the distal end zone of the catheter shaft is usable to irrigate the arterial lumen. It is an advantage of these embodiments that the fluid occupying the lumen may be flushed to minimize scattering of optical radiation by blood cells.

In the above or alternative embodiments of the intravascular catheter system, the working element includes a number of opening members projecting from the distal end of the catheter shaft. The opening members are brought into contact with the occlusion and are operated mechanically by sliding one or more shafts disposed within the catheter shaft, whereupon the tissues of the occlusion are urged apart. It is an advantage of these embodiments that the tissues of the occlusion may be blunt-dissected, separated, or fractured without relying on a cutter or ablation device.

The intravascular catheter system may take various forms comprising some of the above embodiments. For example, the steering apparatus may comprise one or more removable steering shafts disposed within one or more lumina of the catheter shaft or, alternatively, may comprise one or more pulling wires disposed in lumina of the catheter shaft. It is an advantage of a steering shaft or shafts that the steering apparatus can conveniently be introduced into the catheter shaft or interchanged with other apparatus at any time it becomes desirable to do so.

In another exemplary embodiment, the imaging member comprises an imaging shaft disposed in a lumen of the catheter shaft or it may alternatively comprise one or more optical fibers disposed in lumina of the catheter shaft. As an additional exemplary embodiment, the imaging member and steering apparatus may be disposed together in a shaft which is introduced into a lumen of the catheter shaft and which itself has a lumen for accommodating an occlusion crossing wire or guidewire. It is an advantage of this exemplary embodiment that the imaging member is steered along with the occlusion crossing wire or guidewire close to the point of impingement upon the occlusion.

In another exemplary embodiment, the imaging member conducts optical radiation at wavelengths outside the visible spectrum and comprises optical radiation directing paths other than optical fibers. The optical instruments employed in connection with the imaging member may embody a great variety of technologies for extracting information about the environment of the distal end of the intravascular catheter system, including but not limited to the distance, size, shape, orientation, color, fluorescence, motion, composition, metabolism, and the like of objects or tissues.

In another exemplary embodiment, the working element comprises a wide variety of mechanical, thermal, optical, ultrasonic or chemical working elements for crossing the occlusion or delivering a medicament.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein.

DETAILED DESCRIPTION OF THE INVENTION

Figure 1:
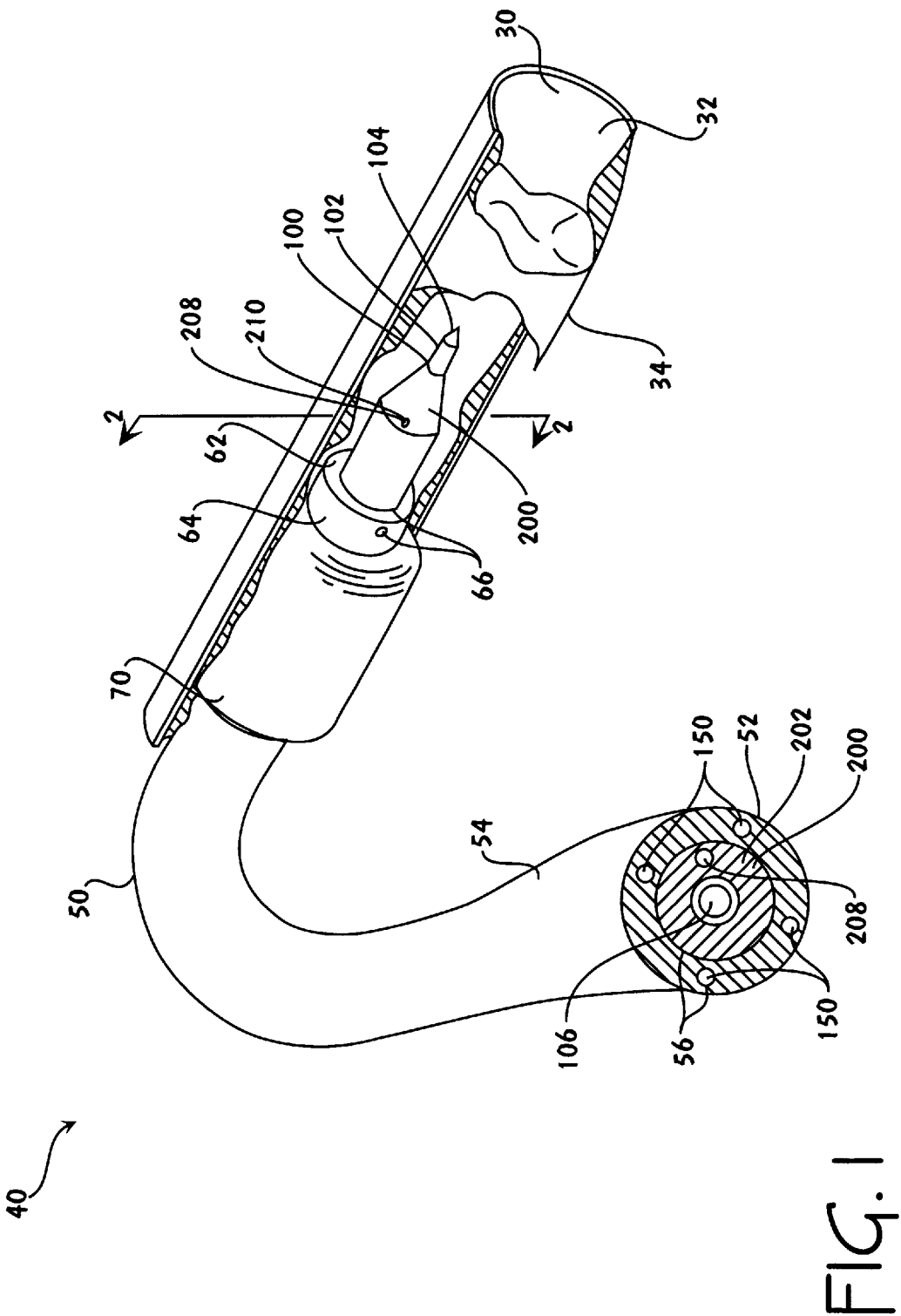
FIG. 1 is a perspective of a first embodiment of the intravascular catheter system including a rotating imaging shaft, the distal end of the system being positioned proximate an occlusion within an artery.

The invention will now be described with respect to the drawings, wherein FIG. 1 illustrates an exemplary embodiment of the intravascular catheter system shown generally by the numeral 40 positioned near an occlusion 34 in the lumen 32 of an artery 30. The intravascular catheter system 40 includes a combination, within a catheter shaft 50, of a working element 100 for crossing the occlusion, a steering apparatus 150 for guiding the working element to a selected part of the occlusion and an imaging member 200 for imaging the arterial wall and occlusion while guiding and operating the working element.

With particular reference to FIG. 1, there is shown the intravascular catheter system which includes an elongated flexible intravascular catheter shaft 50. The proximal end 52 and end zone 54 of the catheter shaft 50 typically remain outside the patient's body and are adapted for convenient connection to external equipment. External equipment may include, generally, handles, torquers, plungers, fluid systems, optical and electrical instruments, and rotating shafts. Running substantially the length of the catheter shaft are a plurality of passages called lumina 56 (plural of "lumen") for the disposition, introduction or control of the working element, the steering apparatus, and the imaging member. At the proximal end of the catheter shaft or close to the proximal end (i.e., in the proximal end zone), the lumina originate in orifices permitting the working element, steering apparatus and imaging member to be connected to external equipment. At the distal end 62 of the catheter shaft or close to the distal end (i.e., in the distal end zone 64), the lumina terminate in orifices 66 allowing the working element and imaging member access to the surrounding environment within the artery and also allowing the introduction of fluids if desired.

Figure 2:
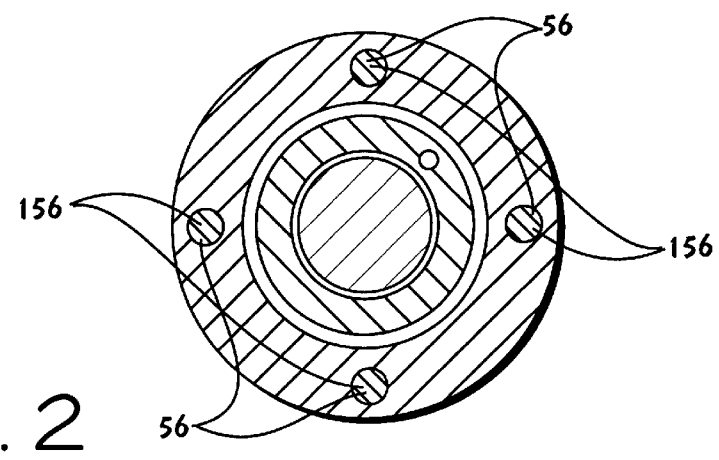
FIG. 2 is a front sectional view of the first exemplary embodiment of the intravascular catheter system.
Figure 3:
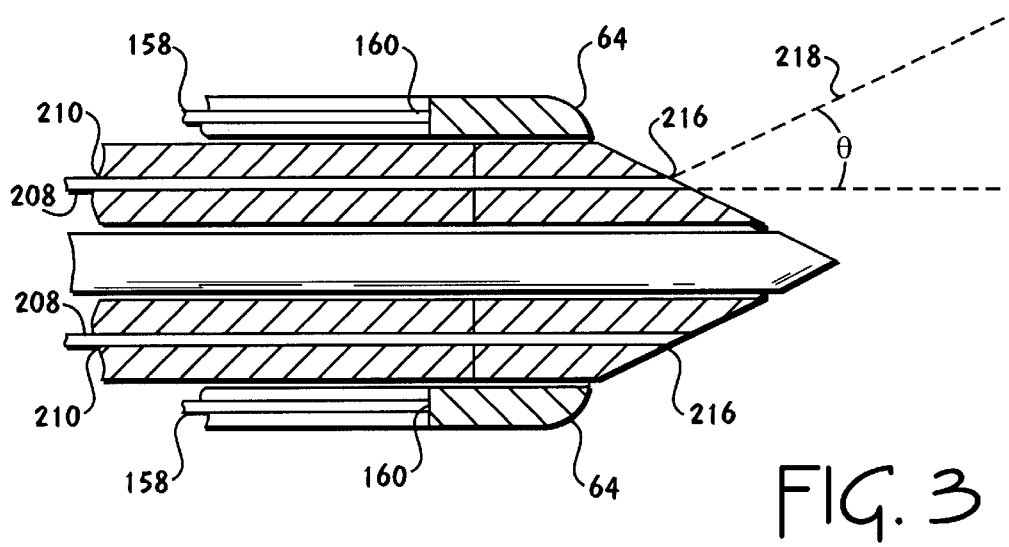
FIG. 3 is a side sectional view of the first exemplary embodiment of the intravascular catheter system.

Referring again to FIG. 1, there is shown a steering apparatus 150 disposed within the catheter shaft for guiding the working element and imaging member within the artery. Referring now to FIG. 2, the steering apparatus comprises at least one pulling wire 156 disposed in at least one lumen 56 of the catheter shaft. Referring to FIG. 3, the pulling wire has a proximal end 158 manipulable from the proximal end of the catheter shaft and a distal end 160 fixed in the distal end zone 64 of the catheter shaft at some radius from the longitudinal axis thereof, so that, when pulled, the wire urges or bends the distal end of the catheter shaft radially (i.e., deviating from the longitudinal axis of the steering shaft). In operation, the pulling wire or wires are manipulated, singly or in combination, to steer the distal end or end zone of the catheter shaft within the artery and thus to steer the working element and imaging member.

Figure 4:
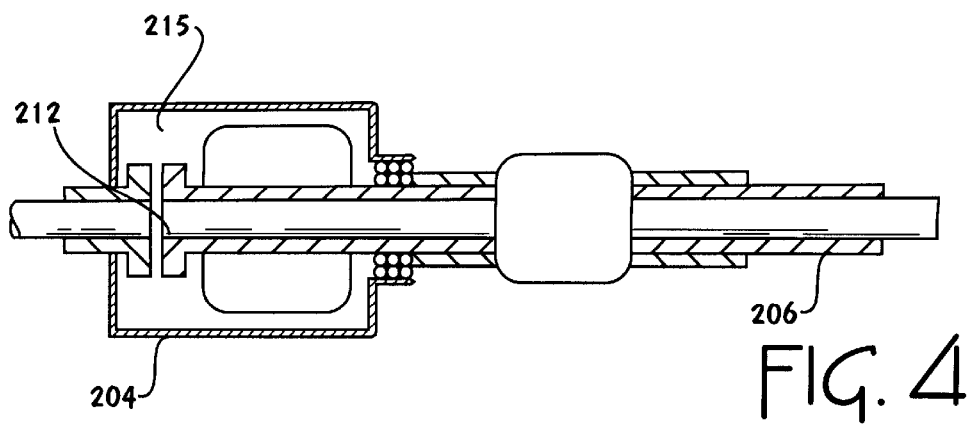
FIG. 4 is a side sectional view of the proximal end zone of the first exemplary embodiment of the intravascular catheter system showing the catheter shaft with shaft motor-encoder assembly and rotating connector.

Referring back to FIG. 1, the intravascular catheter system comprises an imaging member 200 disposed in the catheter shaft 50. The imaging member comprises an elongated, flexible imaging shaft 202 rotatably disposed in a lumen of the catheter shaft. Referring now to FIGS. 3 and 4, a hollow shaft motor-encoder 204 is connected to the proximal end zone 206 (i.e., near the proximal end) of the imaging shaft. At least one optical fiber 208 is disposed within a lumen 210 of the imaging shaft. The optical fiber has a proximal end 212 optically connectable to external instruments 214 through a rotating connector 215 and a distal end 216 optically communicating with the environment of the distal end 64 of the catheter shaft. The distal end of the optical fiber is polished to such an angle, and is so disposed at the distal end zone of the intravascular catheter system, that an optical beam 218 emitted from the distal end of the optical fiber is directed at an angle $\theta$ with respect to the longitudinal axis of the intravascular catheter system.

In operation, the external instruments emit optical radiation into the proximal end of the optical fiber. The optical radiation emerges from the distal end of the optical fiber and illuminates a portion of the environment of the distal end zone of the catheter system. Optical radiation returned from the environment, incident upon the distal end of the optical fiber, is directed back to the external instruments where it is detected. The motor-encoder imparts rotation to the imaging shaft and measures that rotation, such that the optical beam sweeps out a circumferential angle about the longitudinal axis of the imaging shaft. The external instruments correlate the optical and rotational data to generate and display an image of the arterial wall or occlusion. The image may be in one, two, or three dimensions and is typically generated by an appropriately programmed general purpose computer which is interfaced with the optical instruments and the motor-encoder. The image may be generated through any of a variety of techniques known in the art. U.S. Pat. Nos. 5,321,501 and 5, 459,570 are incorporated herein by reference for their teachings about the emission, modulation, direction, detection, and processing of optical radiation to characterize, measure, or image bodily tissues.

Referring again to FIG. 1, the working element 100 of the intravascular catheter system comprises a crossing wire 102 for crossing the occlusion. Referring now to FIGS. 2 and 3, the crossing wire has a distal end 104 disposed in the distal end zone 64 of the catheter shaft 50. The distal end of the crossing wire is capable of projecting from the distal end of the intravascular catheter system to contact the occlusion. The proximal end 106 of the crossing wire is manipulable from the proximal end of the catheter system. In operation, pressure is applied to the proximal end of the crossing wire, urging the crossing wire into the occlusion to establish a pathway.

In the treatment of an occlusion using the embodiment of FIG. 1, a puncture is made in a major artery such as, for example, the femoral artery, in a manner typical for intravascular catheterization. Using standard fluoroscopic technique, a guidewire is introduced through the puncture and is advanced and steered to the region of the artery proximal to the stenosis. Before the catheter shaft is inserted into the artery, the proximal end of the guidewire is introduced into the distal orifice of a lumen of the catheter shaft. The catheter shaft containing the imaging member, steering apparatus and working element is advanced over the guidewire until the distal end of the catheter shaft reaches the segment of the artery proximal to the occlusion. The external instruments and motor-encoder are activated. While observing the image of the artery interior, the physician selects a path for crossing the occlusion, steers the working element by manipulating the pulling wire of the steering apparatus, and urges the occlusion crossing wire into the occlusion. By observing the progress of the working element or its effect upon the occlusion and the artery wall, the physician is able to alter or reselect the path for crossing the occlusion and, thereby, to effectively guide the crossing wire across the occlusion.

Figure 5:
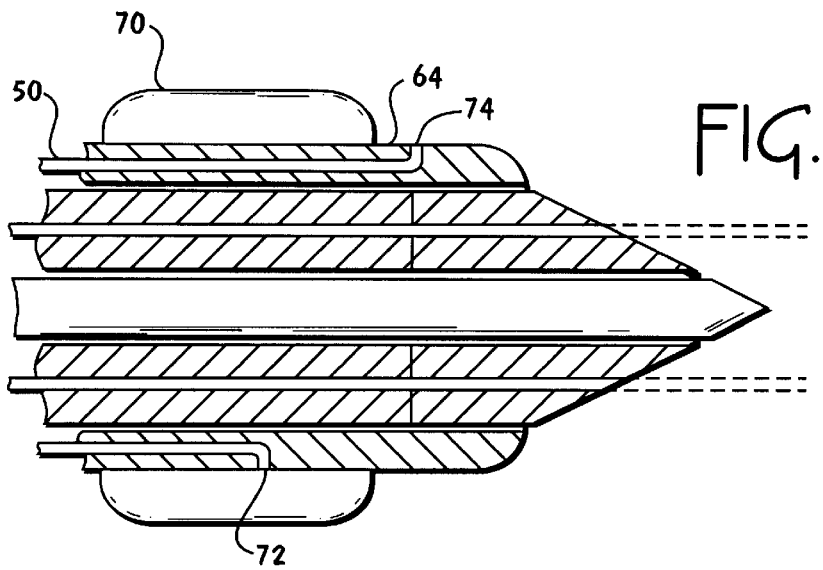
FIG. 5 is a side sectional view of a preferred embodiment of the intravascular catheter system showing the catheter shaft including a balloon and an irrigation lumen.

Referring again to FIG. 1, a preferred embodiment of the intravascular catheter system is shown which comprises at least one balloon 70 disposed at the distal end zone 64 of the catheter shaft 50. Referring now to FIG. 5, the balloon communicates with the distal orifice of at least one balloon inflation lumen 72 of the catheter shaft. The proximal orifice of the balloon inflation lumen communicates with a fluid delivery system at the proximal end of the catheter system. In operation, fluid is introduced through the balloon inflation lumen to inflate the balloon, stabilizing the end zone of the catheter shaft within the artery.

Again referring to FIG. 5, the catheter shaft preferably comprises at least one irrigation lumen 74. The irrigation lumen has a distal orifice located on the outer surface of the distal end zone 64 of the catheter shaft and communicates with the interior of the artery. In embodiments comprising a balloon for stabilizing the distal end zone of the catheter shaft, the distal orifice of the irrigation lumen communicates with the space distal to the balloon. The irrigation lumen has a proximal orifice, located in the proximal end zone of the catheter shaft, communicating with a fluid delivery system. In operation, fluid is introduced and/or removed via the irrigation lumen to clarify an image by removing blood or debris, to establish a fluid current, to apply a medicament, or to withdraw a sample of fluid or tissue as may be desired by the physician.

Figure 6:
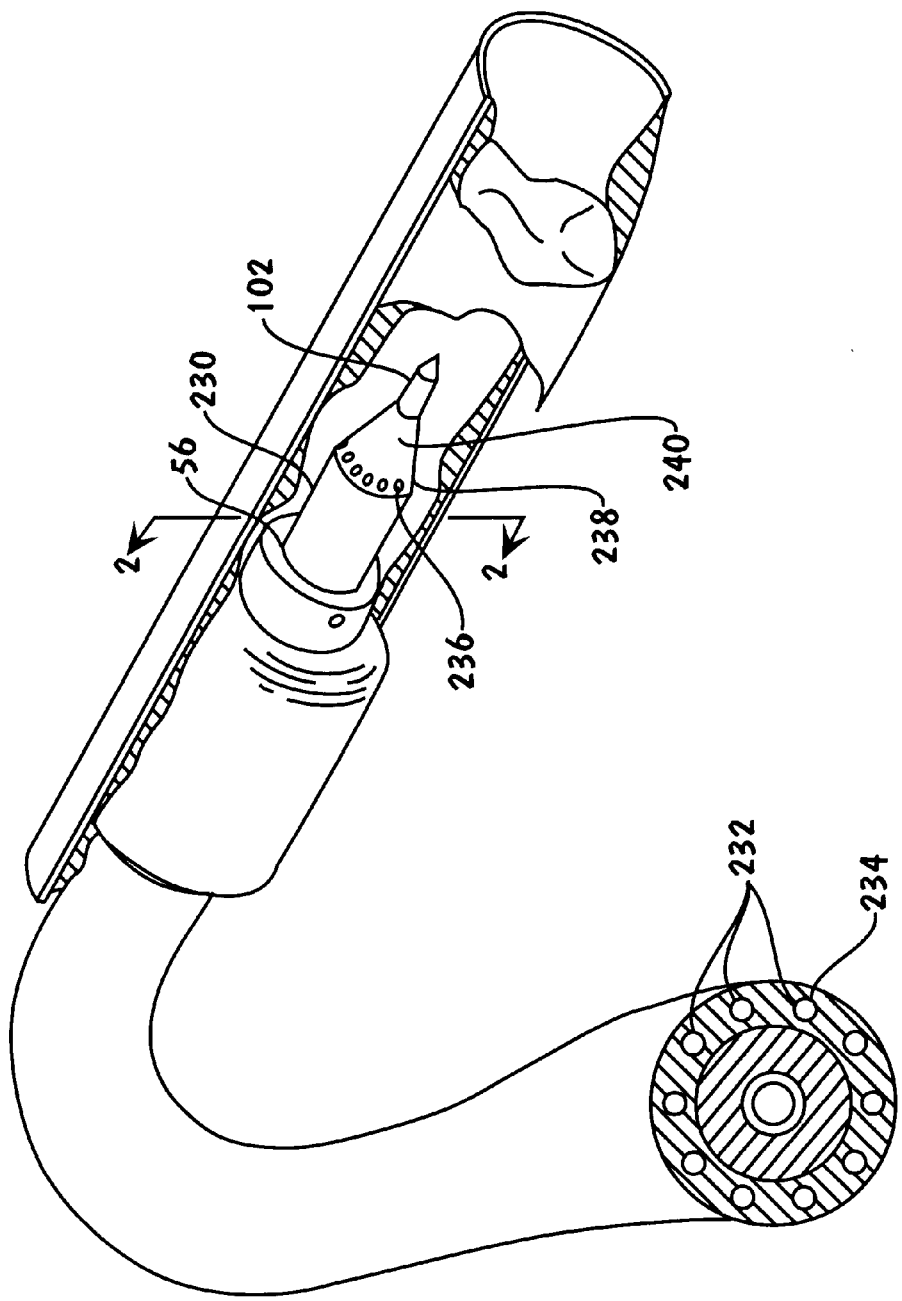
FIG. 6 is a perspective of a second exemplary embodiment of the intravascular catheter system including a plurality of optical fibers disposed in an imaging shaft, the distal end of the system positioned proximate an occlusion within an artery.

Referring now to FIG. 6, a second exemplary embodiment of the invention is shown in which the imaging member comprises an elongated, flexible imaging shaft 230 disposed in a lumen 56 of the catheter shaft. Referring now to FIGS. 6, 7, 8, and 9, a plurality of optical fibers 232 are disposed annularly in the imaging shaft. The proximal ends 234 of the optical fibers are optically connectable to the external instruments. The distal ends 236 of the optical fibers optically communicate with the environment of the distal end zone 64 of the catheter shaft through optical windows 238 in the distal end zone 240 of the imaging shaft. Referring now to FIG. 9, the distal ends of the optical fibers are polished at an angle such that the optical beams 242 emitted therefrom are directed through the optical windows at an angle with respect to the longitudinal axis of the catheter shaft. An optical multiplexer optically connects the proximal ends of the optical fibers to the external instruments.

In operation, the multiplexer selectively optically connects the external instruments to one or more of the optical fibers. The environment of the distal end zone of the imaging shaft is illuminated and optical radiation returning from the environment and incident upon the distal ends of the optical fibers is directed to the external instruments. The external instruments associate data derived from the optical radiation with the relative positions of the optical fibers to generate and display an image of the arterial wall or occlusion. The image may be in one, two, or three dimensions and is typically generated by an appropriately programmed general purpose computer which is interfaced with the optical instruments and the multiplexer. The image may be generated through any of a variety of techniques known in the art. U.S. Pat. Nos. 5,321,501 and 5,459,570 are incorporated herein by reference for their teachings about the emission, modulation, direction, detection, and processing of optical radiation to characterize, measure, or image bodily tissues.

Figure 7:
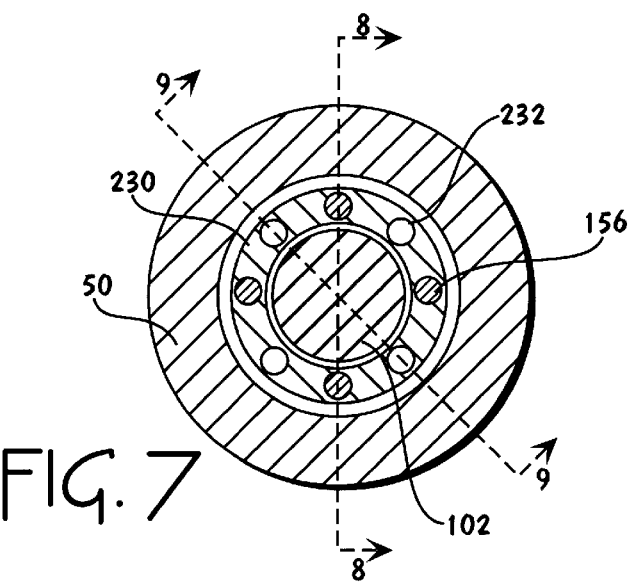
FIG. 7 is a front sectional view of the second exemplary embodiment of the intravascular catheter system.
Figure 8:
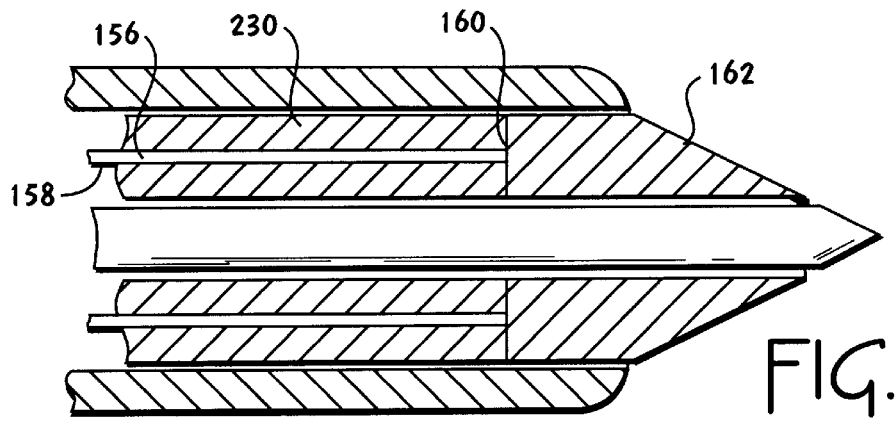
FIG. 8 is a side sectional view of the second exemplary embodiment of the intravascular catheter system in a plane containing points 8—8 shown in FIG. 7.
Figure 9:
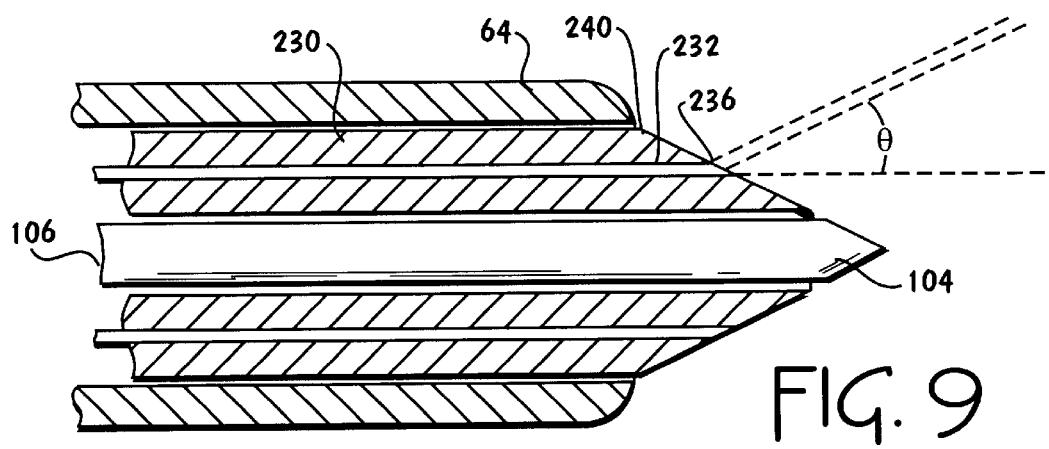
FIG. 9 is a side sectional view of the second exemplary embodiment of the intravascular catheter system in a plane containing points 9—9 shown in FIG. 7.

With reference to FIG. 7 and also to FIG. 8, the above second exemplary embodiment includes a steering apparatus for guiding the imaging shaft and working element 100 within the artery. The steering apparatus comprises at least one pulling wire 156 disposed in the imaging shaft 230. The pulling wire has a proximal end 158 manipulable from the proximal end of the imaging shaft and a distal end 160 fixed to a portion of the distal end zone 162 of the imaging shaft. The distal end of the pulling wire is fixed in the distal end zone of the imaging shaft at some radius from the longitudinal axis so that, when pulled, the wire urges or bends the distal end of the imaging shaft radially (i.e., deviating from the longitudinal axis of the imaging shaft). In operation, singly or in combination, the wire or wires are manipulated to steer the distal end of the imaging shaft. When positioned within the distal end zone of the catheter shaft, the imaging shaft steers the catheter shaft within the artery. To the extent to which the imaging shaft projects distally from the distal end of the catheter shaft, the imaging shaft itself is steerable within the artery with respect to the distal end of the catheter shaft.

Again with reference to FIG. 6, the above second exemplary embodiment includes as its working element an occlusion crossing wire 102 disposed in a lumen of the imaging shaft 230. Referring now to FIGS. 7 and 9, the crossing wire has a distal end 104 disposed in the distal end zone 240 of the imaging shaft 230. The distal end of the crossing wire is capable of projecting from the distal end of the intravascular catheter system to contact the occlusion. The proximal end 106 of the crossing wire is manipulable from the proximal end of the intravascular catheter system. In operation, pressure is applied to the proximal end of the crossing wire, urging the crossing wire into the occlusion to establish a pathway.

In the treatment of an occlusion, the second exemplary embodiment of the intravascular catheter system is introduced and placed proximate the occlusion in the manner recited above for the first exemplary embodiment. The external instruments and optical multiplexer are activated. The occlusion is crossed under optical guidance in the manner recited above for the first exemplary embodiment.

Figure 10:
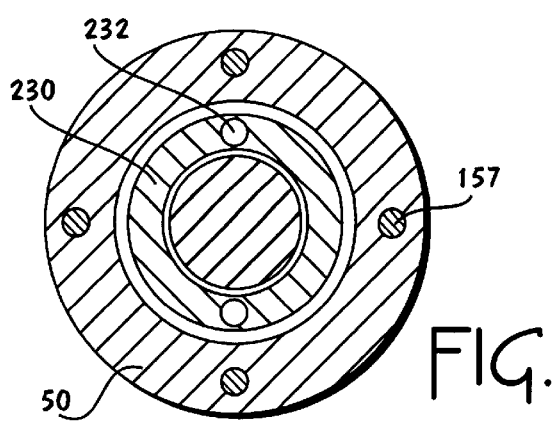
FIG. 10 is a front sectional view of an alternate configuration of the second exemplary embodiment of the intravascular catheter system.
Figure 11:
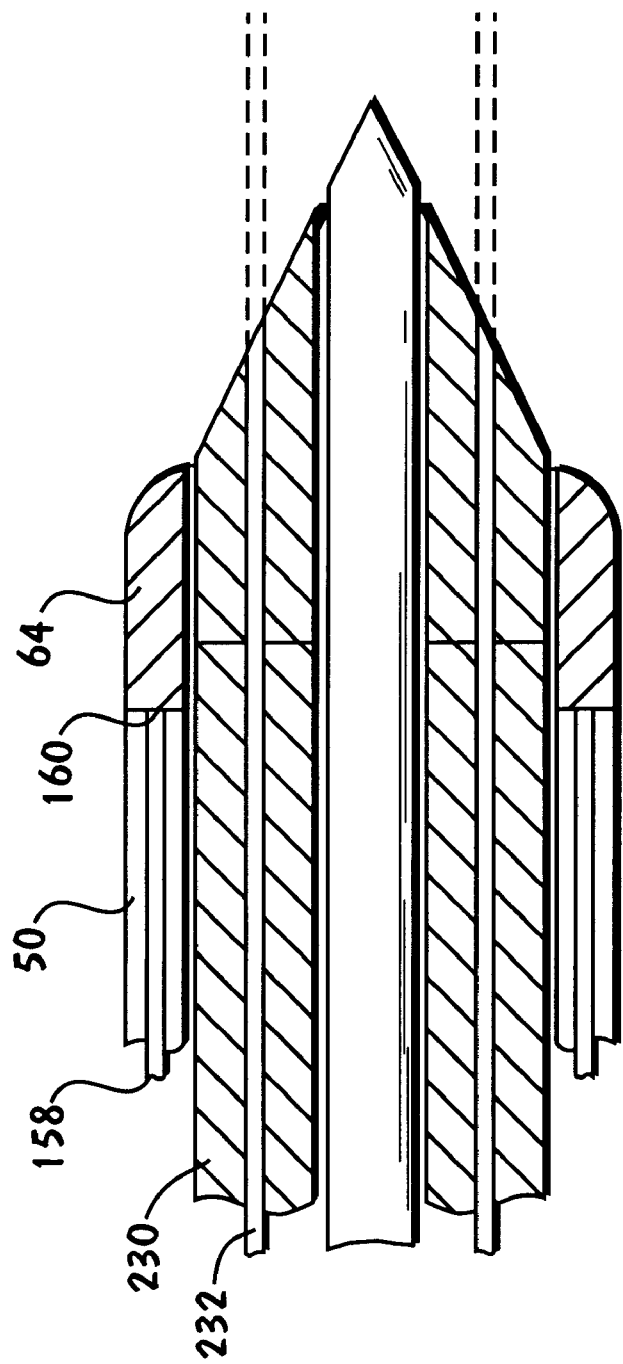
FIG. 11 is a side sectional view of the alternate configuration of the second exemplary embodiment in a plane containing points 11—11 in FIG. 10.

With reference to the second exemplary embodiment of the intravascular system, an alternate configuration is shown in FIGS. 10 and 11. A plurality of optical fibers 232 are disposed annularly within the imaging shaft 230. The steering apparatus comprises at least one pulling wire 157 disposed in a lumen of the catheter shaft 50. The pulling wire has a proximal end 158 manipulable from the proximal end of the catheter shaft and a distal end 160 fixed in the distal end zone 64 of the catheter shaft at some radius from the longitudinal axis thereof, so that, when pulled, the wire urges or bends the distal end of the catheter shaft radially (i.e., deviating from the longitudinal axis of the steering shaft). In operation, the pulling wire or wires are manipulated, singly or in combination, to steer the distal end or end zone of the catheter shaft within the artery and thus to steer the working element and imaging member.

Figure 12:
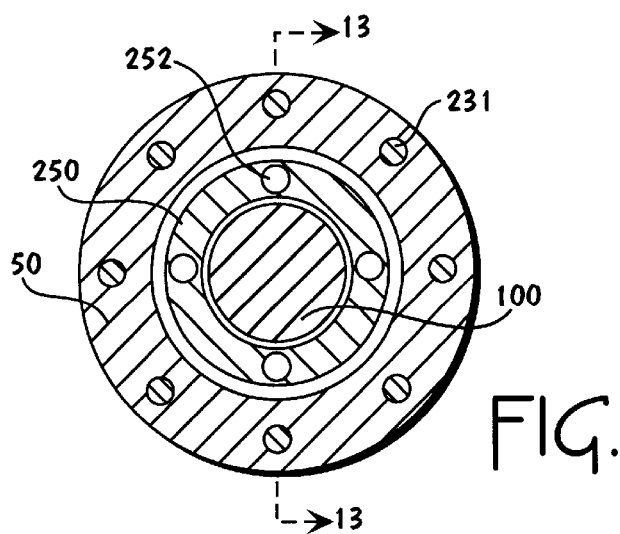
FIG. 12 is a front sectional view of a third exemplary embodiment of the intravascular catheter system.
Figure 13:
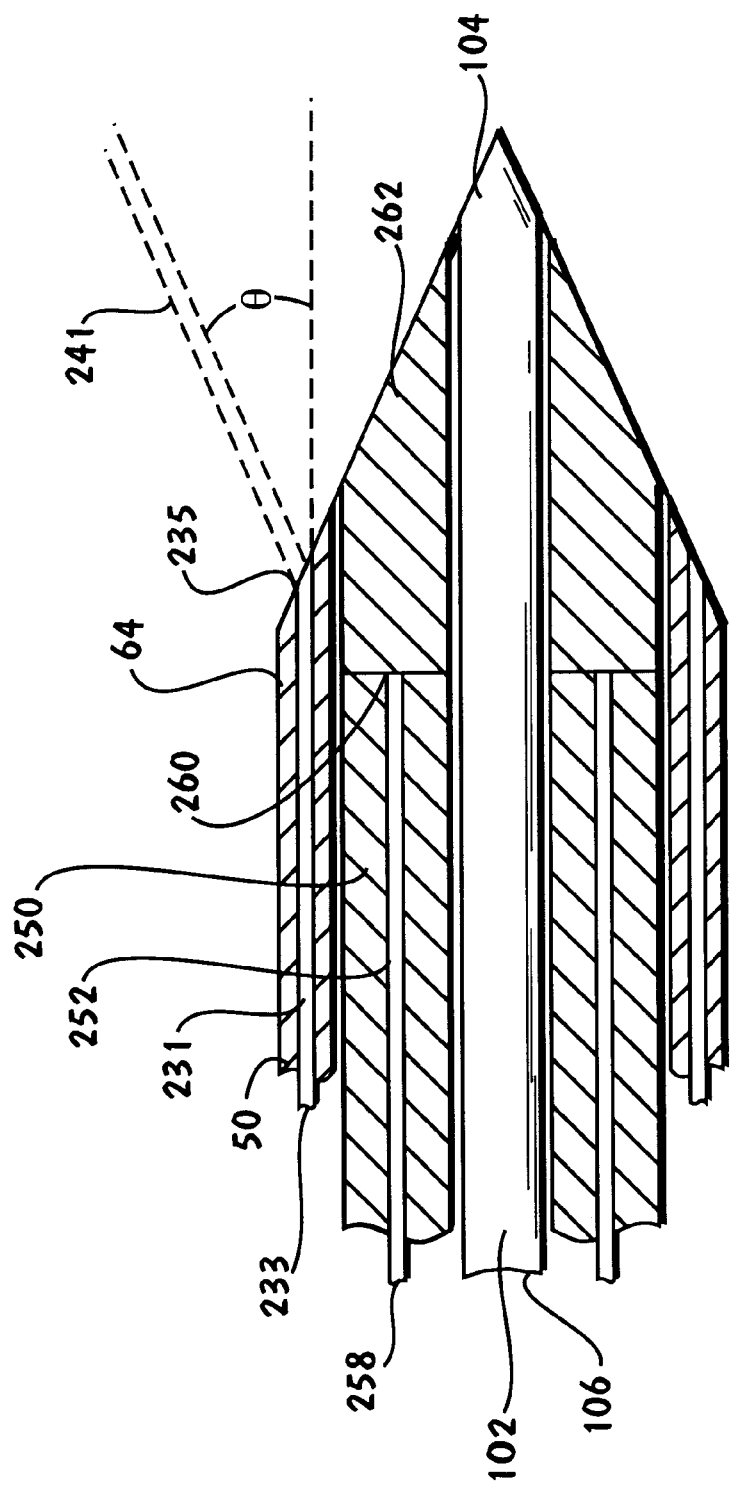
FIG. 13 is a side sectional view of the third exemplary embodiment in a plane containing points 13—13 in FIG. 12.

Referring now to FIGS. 12 and 13, a third exemplary embodiment of the intravascular catheter system is shown in which the imaging member comprises a plurality of optical fibers 231 disposed annularly in lumina of the catheter shaft 50. The proximal ends 233 of the optical fibers are optically connectable to the external instruments. The distal ends 235 of the optical fibers optically communicate with the environment of the distal end zone 64 of the catheter shaft. The distal ends of the optical fibers are preferably polished at an angle such that the optical beams 241 emitted therefrom are directed through the optical windows at an angle with respect to the longitudinal axis of the catheter shaft. An optical multiplexer optically connects the proximal ends of the optical fibers to the external instruments.

Continuing with reference to FIGS. 12 and 13 and the third exemplary embodiment, in operation, the multiplexer selectively optically connects the external instruments to one or more of the optical fibers. The environment of the distal end zone of the imaging shaft is illuminated and optical radiation returning from the environment and incident upon the distal ends of the optical fibers is directed to the external instruments. The external instruments associate data derived from the optical radiation with the relative positions of the optical fibers to generate and display an image of the arterial wall or occlusion. The image may be in one, two, or three dimensions and is typically generated by an appropriately programmed general purpose computer which is interfaced with the optical instruments and the multiplexer. The image may be generated through any of a variety of techniques known in the art. U.S. Pat. Nos. 5,321,501 and 5,459,570 are incorporated herein by reference for their teachings about the emission, modulation, direction, detection, and processing of optical radiation to characterize, measure, or image bodily tissues.

Continuing with reference to FIGS. 12 and 13, the third exemplary embodiment includes a steering apparatus for guiding the working element 100 within the artery. The steering apparatus comprises an elongated, flexible, hollow steering shaft 250 disposed in a lumen of the catheter shaft 50. At least one pulling wire 252 is disposed in the steering shaft. The pulling wire has a proximal end 258 manipulable from the proximal end of the steering shaft and a distal end 260 fixed to a portion of the distal end zone 262 of the steering shaft. The distal end of the pulling wire is fixed in the distal end zone of the steering shaft at some radius from the longitudinal axis so that, when pulled, the wire urges or bends the distal end of the steering shaft radially (i.e., deviating from the longitudinal axis of the steering shaft). In operation, singly or in combination, the wire or wires are manipulated to steer the distal end of the steering shaft. When positioned within the distal end zone of the catheter shaft, the steering shaft steers the catheter shaft within the artery. To the extent to which the steering shaft projects distally from the distal end of the catheter shaft, the steering shaft itself steers within the artery with respect to the distal end of the catheter shaft.

With reference to FIG. 13, the third exemplary embodiment includes as its working element an occlusion crossing wire 102 disposed in a lumen of the steering shaft 250. The crossing wire has a distal end 104 disposed in the distal end zone 262 of the steering shaft. The distal end of the crossing wire is capable of projection from the distal end of the intravascular catheter system to contact and cross the occlusion. The proximal end 106 of the crossing wire is manipulable from the proximal end of the intravascular catheter system. In operation, pressure is applied to the proximal end of the crossing wire, urging the crossing wire into the occlusion to establish a pathway.

Figure 14:
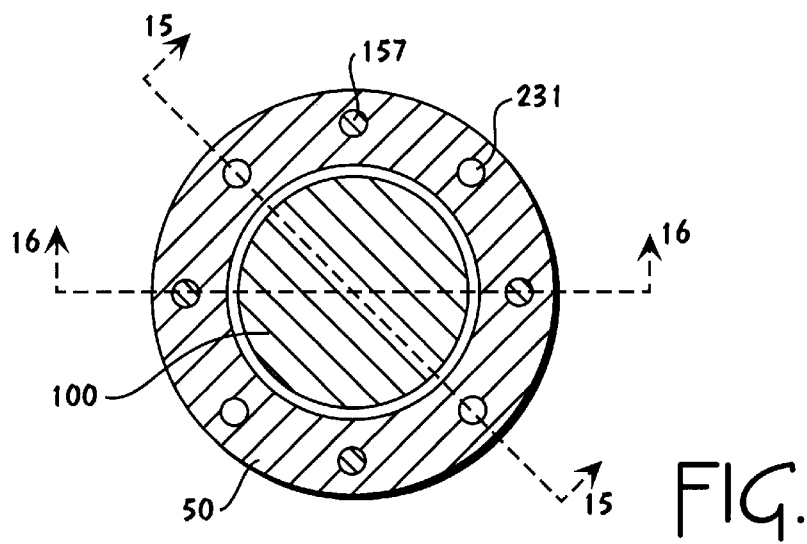
FIG. 14 is a front sectional view of an alternative configuration of the third exemplary embodiment of the intravascular catheter system.
Figure 15:
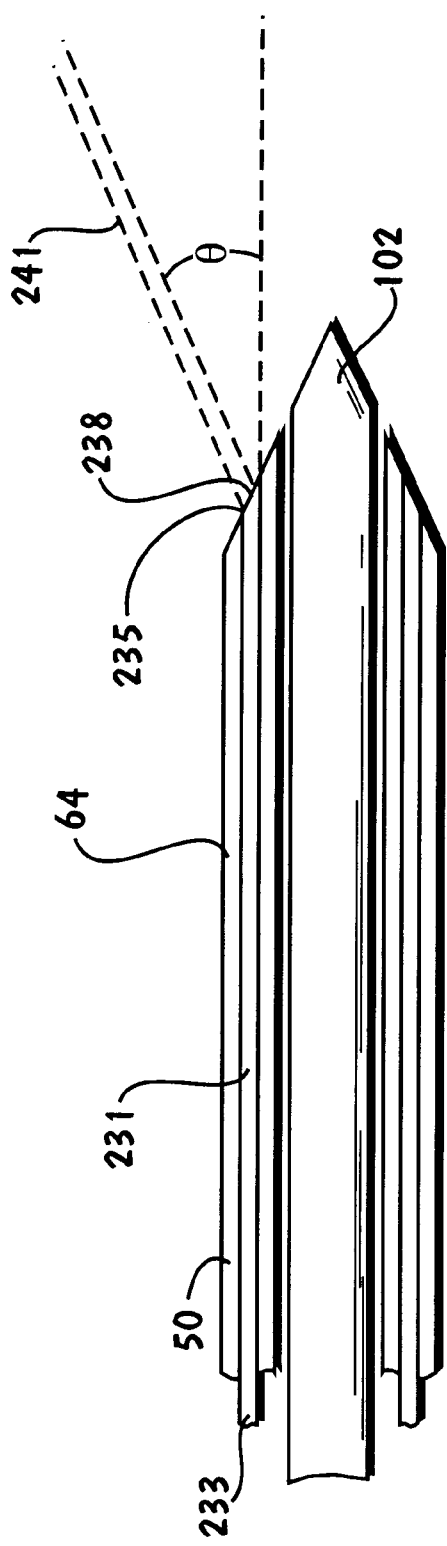
FIG. 15 is a side sectional view of the alternative configuration of the third exemplary embodiment in a plane containing points 15—15 in FIG. 14.
Figure 16:
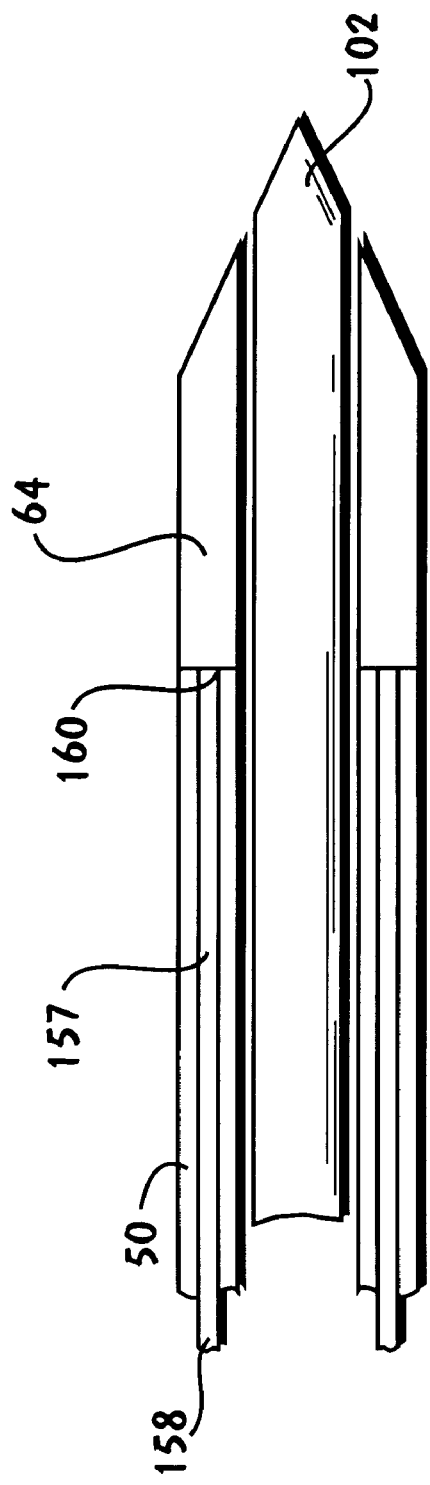
FIG. 16 is a side sectional view of the alternative configuration of the third exemplary embodiment in a plane containing points 16—16 in FIG. 14.

With reference to the third exemplary embodiment, an alternative configuration is shown in FIGS. 14, 15, and 16 wherein the steering apparatus comprises at least one pulling wire 157 disposed in a lumen of the catheter shaft 50. The pulling wire has a proximal end 158 manipulable from the proximal end of the catheter shaft and a distal end 160 fixed in the distal end zone 64 of the catheter shaft at some radius from the longitudinal axis thereof, so that, when pulled, the wire urges or bends the distal end of the catheter shaft radially (i.e., deviating from the longitudinal axis of the steering shaft). In operation, the pulling wire or wires are manipulated, singly or in combination, to steer the distal end or end zone of the catheter shaft within the artery and thus to steer the working element and imaging member. A plurality of optical fibers 231 are disposed annularly in lumina of the catheter shaft 50. The alternative configuration of FIGS. 14, 15, and 16 comprises an occlusion crossing wire 102 disposed in a lumen of the catheter shaft 50.

Figure 17:
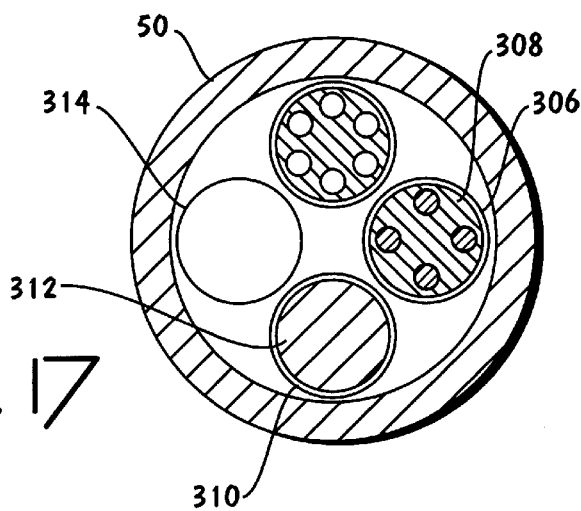
FIG. 17 is a front sectional view of a fourth exemplary embodiment of the invention showing a catheter shaft including four separate lumina.

Referring now to FIG. 17, a fourth exemplary embodiment of the intravascular catheter system is shown wherein the catheter shaft 50 includes a first lumen 302 with imaging shaft 304 disposed therein, a second lumen 306 with steering shaft 308 disposed therein, and a third lumen 310 with working element 312 disposed therein. An inflatable balloon is preferably disposed on the external surface of the catheter shaft about the distal end zone thereof. The catheter shaft preferably comprises a balloon inflation lumen (not shown) communicating with the balloon and an irrigation lumen 314 terminating in an orifice on the external surface of the distal end zone of the catheter shaft distal to the balloon.

Referring generally to FIGS. 1–17, it will be appreciated that the steering apparatus may comprise a plurality of pulling wires and that the pulling wires may be disposed in the catheter shaft itself, in an imaging shaft, or, in a separate steering shaft disposed in a lumen of the catheter shaft. It is envisioned that the cooperation of the elements of the intravascular catheter system to achieve the objects of the invention may include many combinations of pulling on one or more pulling wires, rotating, advancing, or withdrawing the steering shaft, and rotating, advancing, or withdrawing the catheter shaft, imaging member, or working element. Where a steering shaft is disposed in a lumen of the catheter shaft, it is contemplated that the steering shaft might be fixed within the lumen of the catheter shaft, or rotatably disposed therein, or slidably disposed therein; and that the steering shaft might be incorporated into the catheter shaft at assembly, or might instead be introduced later or even after the catheter shaft is placed in the patient. Finally, it will be seen that the steering apparatus may be disposed along with the optical fibers of the imaging member either in the imaging shaft or in the catheter shaft.

With reference to the various embodiments of the intravascular catheter system, it will be appreciated that guidance of the working element may be facilitated by the display of various types of optically derived information about the environment of the distal end zone of the intravascular catheter system. For example, not only the shape and position of tissues, but also their texture, color, reflectivity, or other optically ascertainable physical or biological characteristics may aid the physician in selecting a path across the occlusion. It will also be appreciated that there are many ways of analyzing the raw optical data collected by the imaging member, some of them subtle and mathematically sophisticated. For example, modulation and filtering techniques characterized as spatial, temporal, phase, frequency, coherence, wavelength-dependent, or as relating to polarization, transmission mode, fluorescence, scattering, coefficient of total attenuation, or the like are disclosed in the relevant art. U.S. Pat. Nos. 5,383,467 and 5,439,000 are incorporated herein by reference for their teachings relative to diagnostic techniques based on optical energy. In achieving its objects, the present invention is not intended to be construed as limited to any particular technique for image processing or display.

Also with reference to the various embodiments of the intravascular catheter system, it will be appreciated that the imaging member may comprise not only optical fibers, but any suitable optical radiation directing path. It is further contemplated that where the imaging member comprises an imaging shaft, the imaging shaft may be disposed in a lumen of the catheter shaft fixedly, slidably, or rotatably; permanently or temporarily; before or after placement of the catheter shaft in the patient, as may be convenient. Furthermore, it is contemplated that the imaging shaft may be disposed in a center lumen of the catheter shaft, or in a lumen not centrally located.

Figure 19:
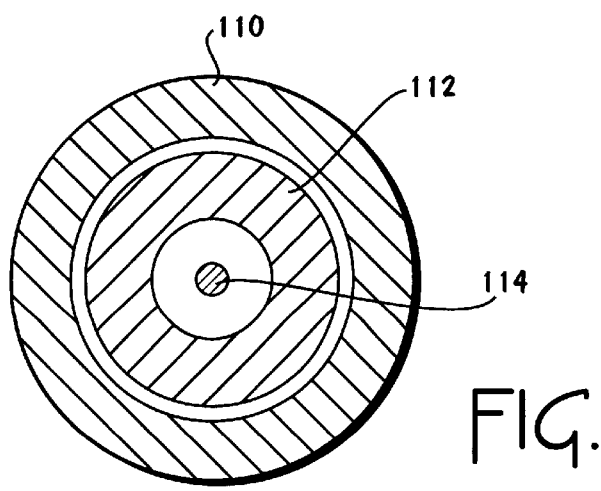
FIG. 19 is a front sectional view of the treatment shaft portion of the working element for the fifth exemplary embodiment of the intravascular system.
Figure 18:
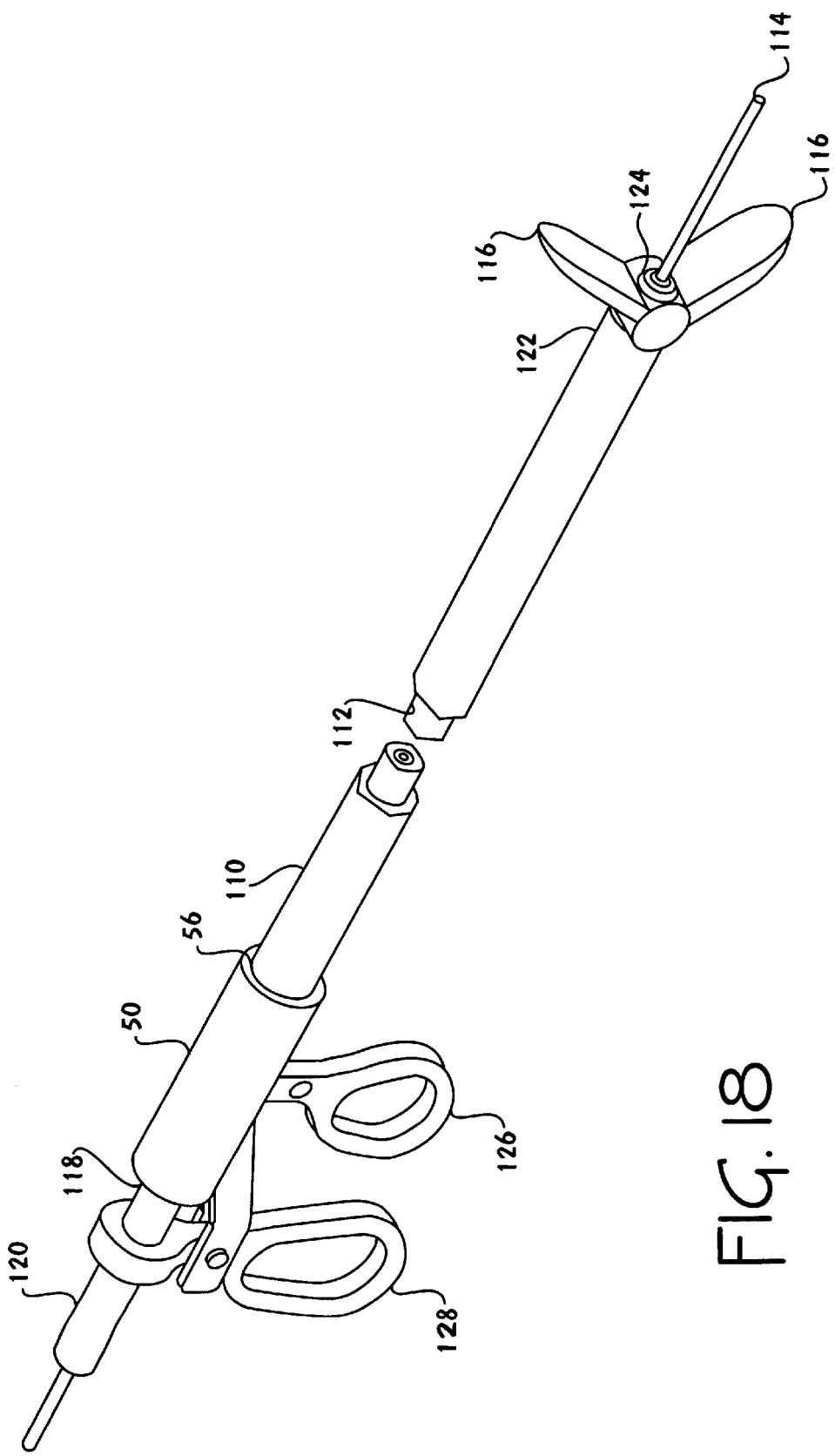
FIG. 18 is a perspective of the working element for a fifth exemplary embodiment of the intravascular catheter system including a plurality of opening members.

Referring now to FIGS. 18 and 19, a fifth exemplary embodiment of the intravascular catheter system is shown wherein the working element comprises a plurality of mechanically operable opening members 116 for urging apart or fracturing the tissues of an occlusion. Elongated flexible outer treatment shaft 110 is disposed in a lumen 56 of the catheter shaft 50 and has a proximal end 118, a distal end 122, and a lumen therebetween. Elongated flexible inner treatment shaft 112 is slidably disposed within a lumen of the outer treatment shaft, and has a proximal end 120, a distal end 124, and a lumen therebetween which accommodates a guidewire 114. The proximal end 118 of the outer treatment shaft and the proximal end 120 of the inner treatment shaft are mechanically manipulable from the proximal end of the catheter shaft. A grip 126 is fixed to the proximal end of the outer treatment shaft. A plunger 128 is fixed to the proximal end of the inner treatment shaft.

Continuing with reference to FIG. 17, a plurality of opening members 116 are movably disposed at the distal ends of the inner and outer treatment shafts such that the opening members are movable in response to relative motion of the inner and outer treatment shafts. The opening members are capable of closing in a flush position about the guidewire such that the inner and outer treatment shafts and opening members can be introduced over the guidewire while the guidewire is within a lumen of the catheter shaft. In operation, the guidewire is advanced into contact with the occlusion. The opening members, in a closed position, are advanced over the guidewire into contact with the occlusion. Through manipulation of the grip and plunger, mechanical force is applied to the proximal ends of the inner and outer treatment shafts, urging the opening members apart. The opening members urge apart the tissues of the occlusion.

With reference to the various embodiments of the intravascular catheter system as described above and as illustrated in FIGS. 1–19, it will be appreciated that the term "working element" is intended to have broad construction and may comprise, by way of example and not of limitation, any of the following: an occlusion crossing wire or trocar tip, a rotary cutting or abrasive nose cone, a balloon, a laser energy delivering device, an ultrasound energy delivering device, a heat delivering device, a blunt dissection device. The structural interrelations between the working element and the catheter shaft may vary depending on the nature of the working element, so long as effective guidance of the working element to establish a path across the occlusion is achievable. Moreover, where the working element comprises a discrete shaft, that shaft may be disposed in a center lumen of the catheter shaft or in a lumen not centrally located, and may be introduced therein either before or after placement of the catheter shaft in the patient.

While the foregoing detailed description has described several embodiments of the method in accordance with this invention, it is to be understood that the above description is illustrative only and not limiting of the disclosed invention. It will be appreciated that the embodiments discussed above and the virtually infinite embodiments that are not mentioned could easily be within the scope and spirit of this invention. Thus, the invention is to be limited only by the claims as set forth below.

What is claimed is:

1. An intravascular catheter system for treating a vascular occlusion, comprising:

an elongated flexible catheter shaft having a proximal end, a distal end, a plurality of lumina therebetween, a proximal end zone, and a distal end zone;

a steering apparatus for steering the distal end zone of the catheter shaft;

an imaging member within the catheter shaft for acquiring an image of a vessel interior proximate the distal end of the catheter shaft, wherein the imaging member comprises an elongated flexible imaging shaft, rotatably disposed within a lumen of the catheter shaft and being capable of advancement at least to the distal end zone thereof, having a proximal end, a distal end, a proximal end zone, and a distal end zone, wherein the imaging member further comprises a hollow shaft motor and rotational encoder attached to the imaging shaft in the proximal end zone thereof for imparting rotation to and measuring rotation of the flexible imaging shaft; and a working element disposed in the distal end zone of the catheter shaft for treating the occlusion, wherein the working element is effectively manipulable and directable at a vascular occlusion while the occlusion is imaged.

2. The intravascular catheter system of claim 1, wherein the imaging member further comprises:

at least one distal optical window in the distal end zone of the flexible imaging shaft; and at least one optical fiber disposed within the imaging shaft, having a proximal end optically connectable to external instruments and a distal end terminating proximate the distal optical window of the imaging shaft, the distal end of the fiber being so disposed within the imaging shaft, and polished at such an angle with respect to the longitudinal axis of the fiber, as to direct an optical beam emitted therefrom through the distal optical window at an angle with respect to the longitudinal axis of the imaging shaft and at an azimuthal angle dependent upon the rotational position of the imaging shaft.

3. The intravascular catheter system of claim 2, wherein the catheter shaft comprises:

an outer surface, at least one lumen terminating in a lateral orifice on an outer surface of the catheter shaft in the distal end zone thereof, at least one balloon disposed on an outer surface of the catheter shaft in the distal end zone thereof and communicating with the lateral orifice for stabilizing the distal end zone of the catheter shaft within an artery; and at least one lumen, terminating in an orifice on an outer surface of the catheter shaft distal to the balloon, for irrigating the environment of the distal end of the catheter shaft.

4. The intravascular catheter system of claim 2 wherein the working element comprises an occlusion crossing wire having distal end introducible via the proximal end of the intravascular catheter system and capable of projecting distally from the distal end thereof, and a proximal end manipulable from the proximal end zone of the intravascular catheter system.

5. The intravascular catheter system of claim 1, wherein the imaging member further comprises:

at least one distal optical window in an outer surface of the distal end zone of the flexible imaging shaft, a plurality of optical fibers disposed within the imaging shaft, each fiber having a proximal end optically connectable to external instruments and a distal end disposed in the distal end zone of the imaging shaft, the distal end of each optical fiber being so disposed within the imaging shaft, and polished at such an angle with respect to the fiber, as to direct an optical beam emitted therefrom through the distal optical window at an angle with respect to the longitudinal axis of the imaging shaft; and an optical multiplexer optically connected to the proximal ends of the optical fibers for selectively optically connecting the proximal ends of the optical fibers to the external instruments.

6. The intravascular catheter system of claim 5 wherein the steering apparatus comprises at least one pulling wire, the wire having a distal end fixed in the distal end zone of the imaging shaft and a proximal end manipulable from the proximal end of the imaging shaft.

7. The intravascular catheter system of claim 6 wherein the working element comprises:

an elongated flexible outer treatment shaft, introducible through a lumen in the catheter shaft from the proximal end zone thereof and capable of advancement to the distal end zone thereof, having a proximal end, a distal end, and at least one lumen therebetween;

an elongated flexible inner treatment shaft disposed within a lumen of the outer treatment shaft and extending substantially the length thereof, having a proximal end, a distal end, and at least one lumen therebetween for allowing the introduction of a guidewire therethrough or the introduction of the treatment shafts over a guidewire;

a plurality of opening members, fixed to the distal ends of the inner and outer treatment shafts, introducible through a lumen in the catheter shaft from the proximal end thereof and slidable and rotatable over a guide wire disposed therein, capable of projecting distally from the distal end of the catheter shaft, closable in a flush position for introduction over a guidewire or through the lumen and openable to urge apart the tissues of an occlusion after being advanced into contact therewith;

an external plunger fixed to the inner treatment shaft near the proximal end thereof; and an external grip fixed to the outer treatment shaft near the proximal end thereof;

wherein the opening members are moved as the plunger is advanced or retracted with respect to the grip; and wherein the working element is effectively directable and manipulable at the vascular occlusion while the occlusion is optically imaged.

8. The intravascular catheter system of claim 5 wherein the steering apparatus comprises at least one pulling wire having a distal end disposed in the distal end zone of the catheter shaft and a proximal end manipulable from the proximal end of the catheter shaft, for steering the distal end of the catheter shaft.

9. The intravascular catheter system of claim 8 wherein the working element comprises:

an elongated flexible outer treatment shaft, introducible through a lumen in the catheter shaft from the proximal end zone thereof and capable of advancement to the distal end zone thereof, having a proximal end, a distal end, and at least one lumen therebetween;

an elongated flexible inner treatment shaft disposed within a lumen of the outer treatment shaft and extending substantially the length thereof, having a proximal end, a distal end, and at least one lumen therebetween for allowing the introduction of a guidewire therethrough or the introduction of the treatment shafts over a guidewire;

a plurality of opening members, fixed to the distal ends of the inner and outer treatment shafts, introducible through a lumen in the catheter shaft from the proximal end thereof and slidable and rotatable over a guide wire disposed therein, capable of projecting distally from the distal end of the catheter shaft, closable in a flush position for introduction over a guidewire or through the lumen and openable to urge apart the tissues of an occlusion after being advanced into contact therewith;

an external plunger fixed to the inner treatment shaft near the proximal end thereof; and an external grip fixed to the outer treatment shaft near the proximal end thereof;

wherein the opening members are moved as the plunger is advanced or retracted with respect to the grip; and wherein the working element is effectively directable and manipulable at the vascular occlusion while the occlusion is optically imaged.

10. The intravascular catheter system of claim 5 wherein the catheter shaft comprises:

an outer surface, at least one lumen terminating in a lateral orifice on an outer surface of the catheter shaft in the distal end zone thereof, at least one balloon disposed on an outer surface of the catheter shaft in the distal end zone thereof and communicating with the lateral orifice for stabilizing the distal end zone of the catheter shaft within an artery; and at least one lumen, terminating in an orifice on an outer surface of the catheter shaft distal to the balloon, for irrigating the environment of the distal end of the catheter shaft.

11. The intravascular catheter system of claim 5 wherein the working element comprises an occlusion crossing wire having distal end introducible via the proximal end of the intravascular catheter system and capable of projecting distally from the distal end thereof, and a proximal end manipulable from the proximal end zone of the intravascular catheter system.

12. The intravascular catheter system of claim 1, wherein the imaging member comprises:

a plurality of optical fibers disposed within the catheter shaft, each fiber having a proximal end optically connectable to external instruments and a distal end disposed in the distal end zone of the catheter shaft, the catheter shaft having at least one distal optical window in an outer surface of the distal end zone thereof, the distal end of each optical fiber being so disposed within the catheter shaft, and polished at such an angle, as to direct an optical beam emitted therefrom through the distal optical window at an angle with respect to the longitudinal axis of the catheter shaft, and at an azimuthal angle unique to each fiber; and an optical multiplexer optically connected to the proximal ends of the optical fibers for selectively optically connecting the proximal ends of the optical fibers to external instruments.

13. The intravascular catheter system of claim 12 wherein the steering apparatus comprises at least one elongated flexible steering shaft, disposed in a lumen of the catheter shaft, having a proximal end, having a distal end having a distal end zone capable of advancement to the distal end zone of the catheter shaft, and having at least one pulling wire, the wire having a distal end fixed in the distal end zone of the steering shaft and a proximal end manipulable from the proximal end of the steering shaft.

14. The intravascular catheter system of claim 13 wherein the working element comprises:

an elongated flexible outer treatment shaft, introducible through a lumen in the catheter shaft from the proximal end zone thereof and capable of advancement to the distal end zone thereof, having a proximal end, a distal end, and at least one lumen therebetween;

an elongated flexible inner treatment shaft disposed within a lumen of the outer treatment shaft and extending substantially the length thereof, having a proximal end, a distal end, and at least one lumen therebetween for allowing the introduction of a guidewire therethrough or the introduction of the treatment shafts over a guidewire;

a plurality of opening members, fixed to the distal ends of the inner and outer treatment shafts, introducible through a lumen in the catheter shaft from the proximal end thereof and slidable and rotatable over a guide wire disposed therein, capable of projecting distally from the distal end of the catheter shaft, closable in a flush position for introduction over a guidewire or through the lumen and openable to urge apart the tissues of an occlusion after being advanced into contact therewith;

an external plunger fixed to the inner treatment shaft near the proximal end thereof; and an external grip fixed to the outer treatment shaft near the proximal end thereof;

wherein the opening members are moved as the plunger is advanced or retracted with respect to the grip; and wherein the working element is effectively directable and manipulable at the vascular occlusion while the occlusion is optically imaged.

15. The intravascular catheter system of claim 12 wherein the steering apparatus comprises at least one pulling wire having a distal end disposed in the distal end zone of the catheter shaft and a proximal end manipulable from the proximal end of the catheter shaft, for steering the distal end of the catheter shaft.

16. The intravascular catheter system of claim 15 wherein the working element comprises:

an elongated flexible outer treatment shaft, introducible through a lumen in the catheter shaft from the proximal end zone thereof and capable of advancement to the distal end zone thereof, having a proximal end, a distal end, and at least one lumen therebetween;

an elongated flexible inner treatment shaft disposed within a lumen of the outer treatment shaft and extending substantially the length thereof, having a proximal end, a distal end, and at least one lumen therebetween for allowing the introduction of a guidewire therethrough or the introduction of the treatment shafts over a guidewire;

a plurality of opening members, fixed to the distal ends of the inner and outer treatment shafts, introducible through a lumen in the catheter shaft from the proximal end thereof and slidable and rotatable over a guide wire disposed therein, capable of projecting distally from the distal end of the catheter shaft, closable in a flush position for introduction over a guidewire or through the lumen and openable to urge apart the tissues of an occlusion after being advanced into contact therewith;

an external plunger fixed to the inner treatment shaft near the proximal end thereof; and an external grip fixed to the outer treatment shaft near the proximal end thereof;

wherein the opening members are moved as the plunger is advanced or retracted with respect to the grip; and wherein the working element is effectively directable and manipulable at the vascular occlusion while the occlusion is optically imaged.

17. The intravascular catheter system of claim 12 wherein the catheter shaft comprises:

an outer surface, at least one lumen terminating in a lateral orifice on an outer surface of the catheter shaft in the distal end zone thereof, at least one balloon disposed on an outer surface of the catheter shaft in the distal end zone thereof and communicating with the lateral orifice for stabilizing the distal end zone of the catheter shaft within an artery; and at least one lumen, terminating in an orifice on an outer surface of the catheter shaft distal to the balloon, for irrigating the environment of the distal end of the catheter shaft.

18. The intravascular catheter system of claim 12 wherein the working element comprises an occlusion crossing wire having distal end introducible via the proximal end of the intravascular catheter system and capable of projecting distally from the distal end thereof, and a proximal end manipulable from the proximal end zone of the intravascular catheter system.

19. The intravascular catheter system for treating a vascular occlusion comprising:

an elongated flexible catheter shaft having a proximal end, a distal end, a plurality of lumina therebetween, a proximal end zone, and a distal end zone;

a steering apparatus for steering the distal end zone of the catheter shaft;

an imaging member within the catheter shaft for acquiring an image of a vessel interior proximate the distal end of the catheter shaft; and a working element disposed in the distal end zone of the catheter shaft for treating the occlusion;

whereby the working element is effectively manipulable and directable at a vascular occlusion while the occlusion is optically imaged, and wherein the working element comprises a plurality of opening members, each of which being projectable distally from the distal end of the catheter shaft and openable to urge apart tissues of an occlusion after being advanced into contact therewith, and wherein the working element comprises:

an elongated flexible outer treatment shaft, introducible through a lumen in the catheter shaft from the proximal end zone thereof and capable of advancement to the distal end zone thereof, having a proximal end, a distal end, and at least one lumen therebetween;

an elongated flexible inner treatment shaft disposed within a lumen of the outer treatment shaft and extending substantially the length thereof, having a proximal end, a distal end, and at least one lumen therebetween for allowing the introduction of a guidewire therethrough or the introduction of the treatment shafts over a guidewire;

a plurality of opening members, fixed to the distal ends of the inner and outer treatment shafts, introducible through a lumen in the catheter shaft from the proximal end thereof and slidable and rotatable over a guide wire disposed therein, capable of projecting distally from the distal end of the catheter shaft, closable in a flush position for introduction over a guidewire or through the lumen and openable to urge apart tissues of an occlusion after being advanced into contact therewith;

an external plunger fixed to the inner treatment shaft near the proximal end thereof; and an external grip fixed to the outer treatment shaft near the proximal end thereof;

whereby the opening members are moved as the plunger is advanced or retracted with respect to the grip; and whereby the working element is effectively directable and manipulable at the vascular occlusion while the occlusion is optically imaged.

20. The intravascular catheter system of claim 19 wherein the catheter shaft comprises:

an outer surface, at least one lumen terminating in a lateral orifice on an outer surface of the catheter shaft in the distal end zone thereof, at least one balloon disposed on an outer surface of the catheter shaft in the distal end zone thereof and communicating with the lateral orifice for stabilizing the distal end zone of the catheter shaft within an artery; and at least one lumen, terminating in an orifice on an outer surface of the catheter shaft distal to the balloon, for irrigating the environment of the distal end of the catheter shaft.

21. An intravascular catheter system for treating a vascular occlusion, comprising:

an elongated flexible catheter shaft having a proximal end, a distal end, a plurality of lumina therebetween, a proximal end zone, and a distal end zone;

a steering apparatus for steering the distal end zone of the catheter shaft;

an imaging member within the catheter shaft for acquiring an image of a vessel interior proximate the distal end of the catheter shaft; and a working element disposed in the distal end zone of the catheter shaft for treating the occlusion;

whereby the working element is effectively manipulable and directable at a vascular occlusion while the occlusion is optically imaged, and wherein the catheter shaft comprises: first, second, and third lumina between the proximal and distal ends of the catheter shaft; a steering apparatus disposed in the first lumen for steering the distal end zone of the catheter shaft; an imaging member disposed in the second lumen for acquiring an image of the vessel interior proximate the distal end of the catheter shaft; and a working element disposed in the third lumen for treating the occlusion; whereby the working element is effectively manipulable and directable at the vascular occlusion while the occlusion is optically imaged, and wherein the working element comprises:

an elongated flexible outer treatment shaft, introducible through a lumen in the catheter shaft from the proximal end zone thereof and capable of advancement to the distal end zone thereof, having a proximal end, a distal end, and at least one lumen therebetween;

an elongated flexible inner treatment shaft disposed within a lumen of the outer treatment shaft and extending substantially the length thereof, having a proximal end, a distal end, and at least one lumen therebetween for allowing the introduction of a guidewire therethrough or the introduction of the treatment shafts over a guidewire;

a plurality of opening members, fixed to the distal ends of the inner and outer treatment shafts, introducible through a lumen in the catheter shaft from the proximal end thereof and slidable and rotatable over a guide wire disposed therein, capable of projecting distally from the distal end of the catheter shaft, closable in a flush position for introduction over a guidewire or through the lumen and openable to urge apart the tissues of an occlusion after being advanced into contact therewith;

an external plunger fixed to the inner treatment shaft near the proximal end thereof; and an external grip fixed to the outer treatment shaft near the proximal end thereof;

whereby the opening members are moved as the plunger is advanced or retracted with respect to the grip; and whereby the working element is effectively directable and manipulable at the vascular occlusion while the occlusion is optically imaged.

22. The intravascular catheter system of claim 21 wherein the catheter shaft comprises an outer surface, at least one lumen terminating in a lateral orifice on an outer surface of the catheter shaft in the distal end zone thereof, and at least one balloon, disposed on an outer surface of the catheter shaft in the distal end zone thereof and communicating with the lateral orifice, for stabilizing the distal end zone of the catheter shaft within a vessel.

23. The intravascular catheter system of claim 21 wherein the catheter shaft comprises at least one lumen, terminating in an orifice on an outer surface of the distal end of the catheter shaft, for irrigating the environment of the distal end of the catheter shaft.

24. The intravascular catheter system of claim 22 wherein the catheter shaft comprises at least one lumen, terminating in an orifice on an outer surface of the catheter shaft distal to the balloon, for irrigating the environment of the distal end of the catheter shaft.

* * * * *